United States Patent
Lamberti et al.

(10) Patent No.: US 9,360,453 B2
(45) Date of Patent: Jun. 7, 2016

(54) INSTRUMENTS FOR MONITORING ELECTROSTATIC PHENOMENA IN REACTORS

(71) Applicants: William Anthony Lamberti, Stewartsville, NJ (US); Joseph Andres Moebus, Houston, TX (US); Harry William Deckman, Clinton, NJ (US); Charles R. Buhler, Cocoa Beach, FL (US); Judson S. Clements, Boone, NC (US); William C. Horn, Long Valley, NJ (US)

(72) Inventors: William Anthony Lamberti, Stewartsville, NJ (US); Joseph Andres Moebus, Houston, TX (US); Harry William Deckman, Clinton, NJ (US); Charles R. Buhler, Cocoa Beach, FL (US); Judson S. Clements, Boone, NC (US); William C. Horn, Long Valley, NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 232 days.

(21) Appl. No.: 14/142,179

(22) Filed: Dec. 27, 2013

(65) Prior Publication Data
US 2014/0193924 A1    Jul. 10, 2014

Related U.S. Application Data

(60) Provisional application No. 61/746,640, filed on Dec. 28, 2012.

(51) Int. Cl.
| | | |
|---|---|---|
| G01N 27/00 | (2006.01) | |
| G01N 27/416 | (2006.01) | |
| G01N 27/60 | (2006.01) | |
| C08F 2/00 | (2006.01) | |
| C08F 2/34 | (2006.01) | |

(52) U.S. Cl.
CPC .............. *G01N 27/60* (2013.01); *C08F 2/002* (2013.01); *C08F 2/34* (2013.01); *C08F 2400/02* (2013.01)

(58) Field of Classification Search
CPC ........... C08F 2/34; C08F 10/00; C08F 2/002; C08F 2400/02; G01N 27/60
USPC ............................................ 436/151; 422/98
See application file for complete search history.

(56) References Cited

U.S. PATENT DOCUMENTS

| | | |
|---|---|---|
| 4,247,299 A | 1/1981 | Klein et al. |
| 5,315,255 A | 5/1994 | Bettinger |
| 6,008,662 A | 12/1999 | Newton et al. |

(Continued)

FOREIGN PATENT DOCUMENTS

| | | |
|---|---|---|
| EP | 0970970 B1 | 12/2003 |
| EP | 1623999 A1 | 2/2006 |

(Continued)

OTHER PUBLICATIONS

The International Search Report and Written Opinion of PCT/US2013/078044 dated Jul. 29, 2014.

(Continued)

*Primary Examiner* — William Cheung
(74) *Attorney, Agent, or Firm* — Robert A. Migliorini

(57) ABSTRACT

Probes for monitoring electrostatic phenomena in challenging environments, such as fluidized bed reactors. These probes include a coated or uncoated static probe for measuring electric field and or particle charge state, an oscillatory electric field probe for measuring electric field, a chopped electric field probe for measuring electric field, and a radio-frequency antenna probe for detecting electrostatic discharges.

26 Claims, 9 Drawing Sheets

(56) References Cited

U.S. PATENT DOCUMENTS

| | | | |
|---|---|---|---|
| 6,506,156 B1 * | 1/2003 | Jones | A61K 49/223 600/432 |
| 6,660,812 B2 | 12/2003 | Kuechler et al. | |
| 6,831,140 B2 | 12/2004 | Muhle et al. | |
| 6,905,654 B2 | 6/2005 | Bartilucci et al. | |
| 7,799,876 B2 | 9/2010 | Markel et al. | |
| 2004/0132931 A1 | 7/2004 | Muhle et al. | |
| 2010/0289482 A1 * | 11/2010 | Markel | B01J 8/1809 324/149 |

FOREIGN PATENT DOCUMENTS

| | | | |
|---|---|---|---|
| EP | 2263993 | A2 | 2/2006 |
| EP | 0784637 | B2 | 3/2008 |
| EP | 2228648 | A2 | 9/2010 |
| WO | 98/12231 | A1 | 3/1998 |
| WO | 0206188 | A2 | 1/2002 |
| WO | 2004060940 | A1 | 7/2004 |
| WO | 2005113615 | A2 | 12/2005 |
| WO | 2008/016478 | A2 | 2/2008 |
| WO | 2009014682 | A2 | 1/2009 |

OTHER PUBLICATIONS

Bahreyni, B. et al., "Design and Testing of a Field-Chopping electric field Sensor using Thermal Actuators with Mechanically amplified Response," Solid State Sensors, Actuators and Microsystems Conference, 2007, pp. 1397-1400.

U.S. Appl. No. 14/141,857, filed Dec. 27, 2013.

* cited by examiner

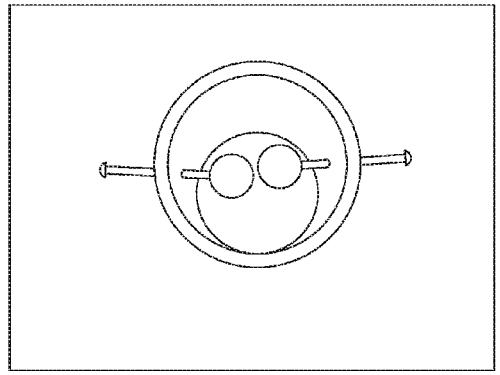 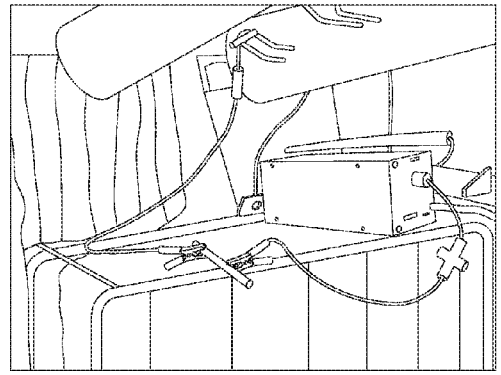
FIG. 12a  FIG. 12b
```
Data File for image_06_Jul_2011_16_37_49
Trigger Type: RF Only
Neither Threshold Triggered and RF
```
FIG. 13

INSTRUMENTS FOR MONITORING ELECTROSTATIC PHENOMENA IN REACTORS

CROSS REFERENCE TO RELATED APPLICATIONS

This application claims priority to U.S. Provisional Application Ser. No. 61/746,640 filed Dec. 28, 2012, herein incorporated by reference in its entirety.

FIELD

The disclosure relates to specialized instruments for measuring and monitoring electrostatic phenomena in complex environments such as those which exist within gas-phase, fluidized bed reactors.

BACKGROUND

Fouling in commercial fluidized bed reactors, including gas phase polymerization reactors, is a significant operational issue. Fouling negatively impact operational efficiency and ultimately requires time-consuming shutdown and maintenance.

Understanding the causal factors of fouling within the reactor systems would be beneficial in reducing fouling. Fouling in fluidized bed reactors can be strongly affected by physical processes within the fluidized bed reactor, such as electrostatic charge and solids carryover within a recycle loop.

Commercial probes, including those commonly referred to as static probes and acoustic probes, exist for measuring certain physical parameters within fluidized bed reactors, such as electrostatic charge and solids flow. In common practice, however, these probes do not reliably directly measure these phenomena, and are instead dominated by noise and/or artifacts in the signals. Thus, probe signals have proven to be of limited or no value in monitoring the operational status of or diagnosing inefficiencies in fluidized bed reactors.

Electrostatic charge can affect commercial process units such as chemical reactors, granular particle handling equipment, transfer lines, holding tanks, and shipping containers, for example. The types of operations can include fluidized bed reactors for producing a variety of chemical products such as gas, liquid or solid products such as polyethylene. Cryogenic processes or handling equipment are another notable case where the dry environment can lend itself to electrostatic charge buildup in at least some portions of a process, especially if solids such as ice form due to the cryogenic conditions. The buildup of electrostatic charge on particles, and/or process components results in the formation of an electric field, which then exerts forces on particles or components within a given process or system. Additionally, in cases where the electrostatic charge is sufficient, electrostatic discharge events can occur, which by themselves can be deleterious to reliable or safe operations, or simply an indicator that electrostatic effects are present at a given moment.

For example, commercial polyethylene (PE) reactors utilize a fluidized bed to suspend catalyst particles that grow into PE resin particles by converting ethylene gas into polyethylene resin. Collisions between catalyst particles, resin particles and also the reactor wall can result in the particles becoming charged. The wall can also become charged wherever it has an insulating coating or surface deposit or layer.

If the net charge per volume ($\rho$) in a cylindrical reactor is uniform, the electric field is given by: $E(r)=(\rho r)/2\in$, where r is the cylinder radius, E(r) is the electric field as a function of reactor vessel radius and $\in$ is the relative permittivity of the volume. This electric field is greatest at the reactor wall, and creates a force (F) on the charged particles given by $F(r)=qE(r)$, where q is the particle charge. Both F and E are still a function of radius as mentioned above.

Particles with charge of the same sign as the bulk net charge density experience a force towards the wall. If this force is large enough, it can pin the charged catalyst and resin particles to the wall, and they tend to grow into PE sheets (sheeting) that eventually fall off and clog up the resin discharge system, forcing a shutdown of the reactor. In addition, if the electric field is larger than the Paschen breakdown strength of the gas in the reactor, electrical discharges, or sparks can occur through the gas. Any isolated conductors in the reactor can become charged by particle impact, and they can also spark to nearby metallic objects. In addition, the insulating coating on the reactor wall can charge to a level that supports propagating brush discharges across and through the wall surface.

It is desirable to instrument the reactor with sensors that can indicate a highly charged condition, because that can eventually lead to sheeting and a forced reactor shutdown. Advanced knowledge of a sheeting condition allows operating parameters to be adjusted to eliminate the condition. A highly charged reactor condition can be accompanied by sparking inside the reactor, while lower levels of charge would not result in sparks. Therefore, sparking can be used as an indicator of a highly charged reactor, and indirectly, as a warning that the reactor is in a condition conducive to sheeting.

It is well known that electrical sparks emit electromagnetic waves, typically in the radio frequency (RF) part of the electromagnetic spectrum between about 100 kHz and 10 GHz. Due to the challenging environments encountered in chemical process equipment, especially within a high temperature fluidized bed with reactive gas mixture, no prior art exists for detection of RF signals arising from electrical discharges. In simpler environments, such as assembly rooms for sensitive semiconductor components, some technology does exist. For these simpler environments, the current art includes technology such as the 3M company's EM Aware[1], which contains radio frequency receivers with appropriate antennas used to detect sparks by receiving these radio waves. The amplitude, spectral distribution and radiation pattern of the emitted waves depends on the source of the spark.

[1] 3M™ EM Aware TNG ESD Event Monitor. Models 3M034-3-TNG, 3M034-030-TNG and 3M034-031-TNG As indicated in the EM Aware user guide published by the manufacturer, this technology is intended to be used only as follows. "Intended Use"—The 3M EM Aware TNG ESD Event Monitor monitors up to four key parameters that keep you aware of critical symptoms of ESD problems: 1) ESD events; 2) static voltages; 3) ionization balance; and 4) charge decay. The thresholds for these parameters are fully adjustable to suit your needs. The improved design features a metal case module with built-in LCD display, a control joystick, remote antenna, power supply and a data output.

The monitor system must be installed as specified in this user's guide. It is intended for use in the following environmental conditions only: (1) indoor use; (2) altitudes up to 2,000 meters above sea level; (3) temperature range of 10° C. to 40° C.; (4) maximum relative humidity of 80% for temperatures up to 31° C., decreasing linearly to 50% relative humidity at 40° C.; and (5) pollution degree two (office, laboratory, test station).

It would be desirable to have instruments which can reliably measure and monitor electrostatic phenomena within these systems. These instruments could also be combined with new methods for processing and interpreting probe signals in fluidized bed reactor systems. It would further be desirable to have new methods, which may rely upon the use of these instruments and processing methods to provide for more efficient system operation and reliability.

SUMMARY

A coated static probe which monitors the electrostatic charge on particles entrained in the gas stream of a vessel, the probe comprising: an electrode, such as a metal rod with a modified surface comprising an electrically insulating coating, thereby mitigating triboelectrification of the probe arising from charge transfer from impinging particulates and extraneous signals via charge saturation of the coating.

The coating is a dielectric material that maintains a saturation charge layer and inhibits tribocharging.

The dielectric material is a high dielectric strength, and high volume and surface resistivity.

The dielectric material is at least one material selected from the group consisting of: polyethylene, polypropylene, polytetrafluoroethylene, polyether ether ketone, aluminum oxide, silicon dioxide, iron oxide, and any other electrically insulating material, such as glasses, ceramics and polymers.

The dielectric material maintains the charge saturation by exhibiting high dielectric strength, and high surface resistivity and high volume resistivity. Additionally, proper relative placement within triboelectric series can help maintain charge saturation.

The dielectric strength determines the maximum electric field at which the material reaches electrical breakdown.

The surface and volume resistivity determine the rate at which a material will discharge analogous to an RC circuit.

The placement within triboelectric series affects the amount and polarity of charge transferred due to contact and separation.

The coating is applied to the static probe by dip coating, for example.

The dip coating comprises the steps of: heating the static probe; submerging the heated static probe into a bed of polymer particles with suitable melting point and adhesive properties, such that the polymer particles adhere to the static probe; heating the static probe after the polymer particles have been adhered thereto to the point where they begin to flow; and once the polymer particles have formed a uniform coating on the static probe, heating is stopped, thereby allowing the coating to harden on the static probe.

A method for monitoring the electrostatic charge on particles entrained in the gas stream of a vessel comprises: disposing the coated static probe within the gas stream of the vessel.

The gas stream is at least one stream selected from the group consisting of: a product discharge stream, a recycle stream, a fluidizing gas stream, a mixing stream, a purge stream, a feed stream, and a transfer stream, for example.

The vessel is at least one vessel selected from the group consisting of: a fluidized bed reactor, a product tank, a purge vessel, a holding vessel, a shipping vessel, a discharge tank, a mixing vessel, piping between the vessels, a shipping vessel, a rail car, and/or a truck.

A coated static probe which monitors the electrostatic charge on particles entrained in the gas stream of a vessel, the probe comprising: a metal electrode, often in the form of a rod, with a modified surface comprising a coating which measures the ambient direct current electric field by periodically blocking the field near the probe while also substantially minimizing particle-to-surface interactions via purging of a sensing element with a flowing gas.

An RF probe which monitors the electrostatic discharges in a vessel, the probe comprising: an antenna; a flange bolted to a mating flange welded on the outside of a wall of the vessel; an electrode, such as a metal rod connected to the antenna, wherein the rod is hermetically sealed by means of an insulating material, thereby electrically isolating the antenna from the flange; an electronics module and a power supply disposed within a pressure containment housing or a separate shielded, cooled external enclosure located outside of the vessel and electronically connected to the rod; and an electrically conductive wire which electronically connects the antenna to the electronics module.

The RF probe further comprises a double pressure containment housing.

The RF probe is a hardened probe comprising: (a) spark detection electronics, or (b) circuitry with high sensitivity and high speed electrical response together with a single channel analyzer and/or frequency based filter circuitry.

The frequency based filter circuitry is at least one selected from the group consisting of: lock-in amplification, Fourier analysis, digital filtering and correlation circuits, integrators, baseline shifters, and averaging circuits.

The probe sensitivity is proportional to the length of the antenna.

The RF probe wherein the wire is a coax cable and the electronics module comprises a receiver/amplifier filter.

A method for monitoring the electrostatic discharges in a vessel which comprises: disposing the RF probe within the gas stream of the vessel.

A probe which monitors the electrostatic state in a vessel, the probe is at least one selected from the group consisting of: a coated or uncoated static probe, an oscillatory electric field probe, a chopped electric field probed, and a radio-frequency antenna probe.

A fluidized bed reactor comprising either a coated static probe or a radio frequency (RF) probe disposed in at least one portion of the fluidized bed reactor selected from the group consisting of: a recycle line, product discharge system, fluid bed, expanded or disengagement zone above the fluidized bed, purge system, and product handling or shipping system.

A stirred, slurry or other type of reactor system with a coated static probe or a radio frequency (RF) probe disposed in the reactor system.

Further according to the present disclosure, there are provided specialized instruments for measuring and monitoring electrostatic phenomena in complex environments, such as those which exist within gas-phase, fluidized-bed reactors.

BRIEF DESCRIPTION OF THE DRAWINGS

FIG. 12*a* is a picture of the spark-gap.

FIG. 12*b* shows a high voltage power supply and the wooden-dowel tera-ohm range adjustable resistor connected to the spark gap.

FIG. 13 is an example of the data acquisition and control program text file output.

DETAILED DESCRIPTION OF THE PREFERRED EMBODIMENTS

Figure 1:
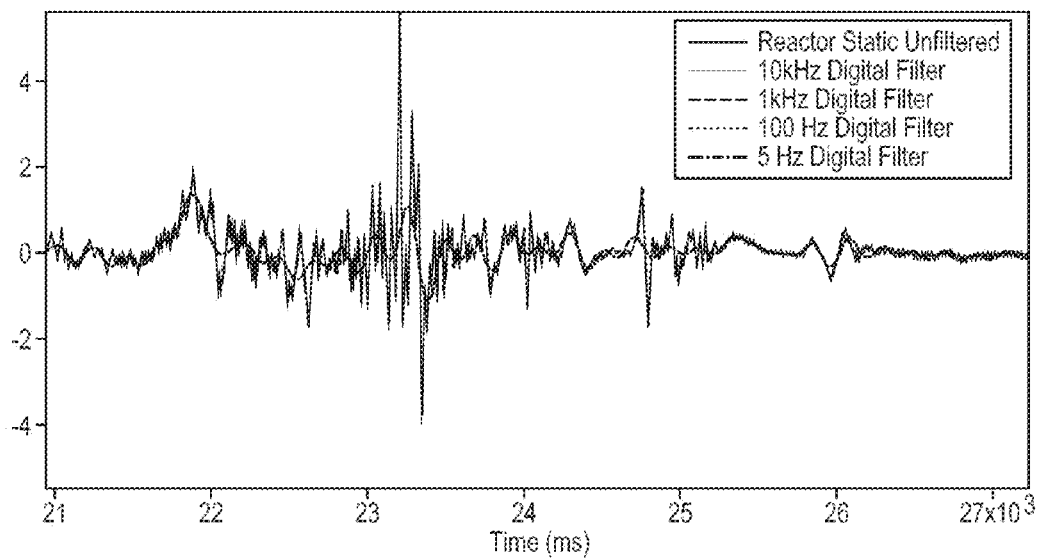
FIG. 1 is a plot of static probe filtered frequency data from the reactor or lower bed.

All numerical values within the detailed description and the claims herein are modified by "about" or "approximately" the indicated value, and take into account experimental error and variations that would be expected by a person having ordinary skill in the art.

In the methods of the disclosure, multiple signal processing and data interpretation techniques, as applied to signals obtained from probes, reveal information about the physics (i.e., electrostatics and solids transfer) within an operating fluidized bed reactor. These techniques, when applied to conventional or modified static probes, can elucidate the electrostatic charge on particles within a fluidized bed system or carryover stream. Additional techniques, when applied to acoustic sensors, can elucidate the rate of solids transfer, flow, and carryover rate in the fluidized system. These techniques, when combined, with or without additional sensor information from the reactor (i.e., valve timings, pressure, gas compositions, etc.), can provide unique information regarding the overall performance and operational status of a fluidized bed reactor system. This information, in turn, affords enhancements in operability and reduction in fouling.

Mathematical techniques can be applied to static and/or acoustic probe data to obtain a variety of useful indicators for reactor conditions. Useful techniques include Fourier analysis, digital filtering of high-speed static probe data (i.e., data sampling rates faster than 10 Hz; 100 Hz is typical), integrations, baseline shifts, time-resolved means and inverse means, time-resolved variances, auto-correlations, cross-correlations, and direct correlations with other sensor information.

Static Probes

Static probes measure current. Sources of current can be direct tribocharging due to particle impact or induced current arising from fluctuations in the electric field. Bare metal static probes signals can be dominated by triboelectric charge transfer via particle collisions, which affects mean and integral values of the static probe signal. Surface-altered static probes have a dielectric coating made from an electrostatically insulating material applied to the sensing tip that mitigates the triboelectric charge transfer. For the coating to be an effective mitigation technique, the coating must reach a state of charge saturation in which further charge transfer is reduced, on average, to an insignificant level. This mitigates direct triboelectric charging. The amount of time the coating takes to reach the charge-saturated state is dependent on the material the coating is made of and the charge transfer rate of the impinging particles. Mitigation of the triboelectric charge transfer and charge injection allows for accurate measurement of the mean and variance of the resultant static probe signal.

The use of static probes in fluidized bed reactor systems is disclosed by way of example in U.S. Pat. No. 6,831,140 B2; 7,799,876 B2; WO 2004/060940; and WO 2009/014682 A2, all of which are incorporated by reference herein in their entireties.

Figure 9:
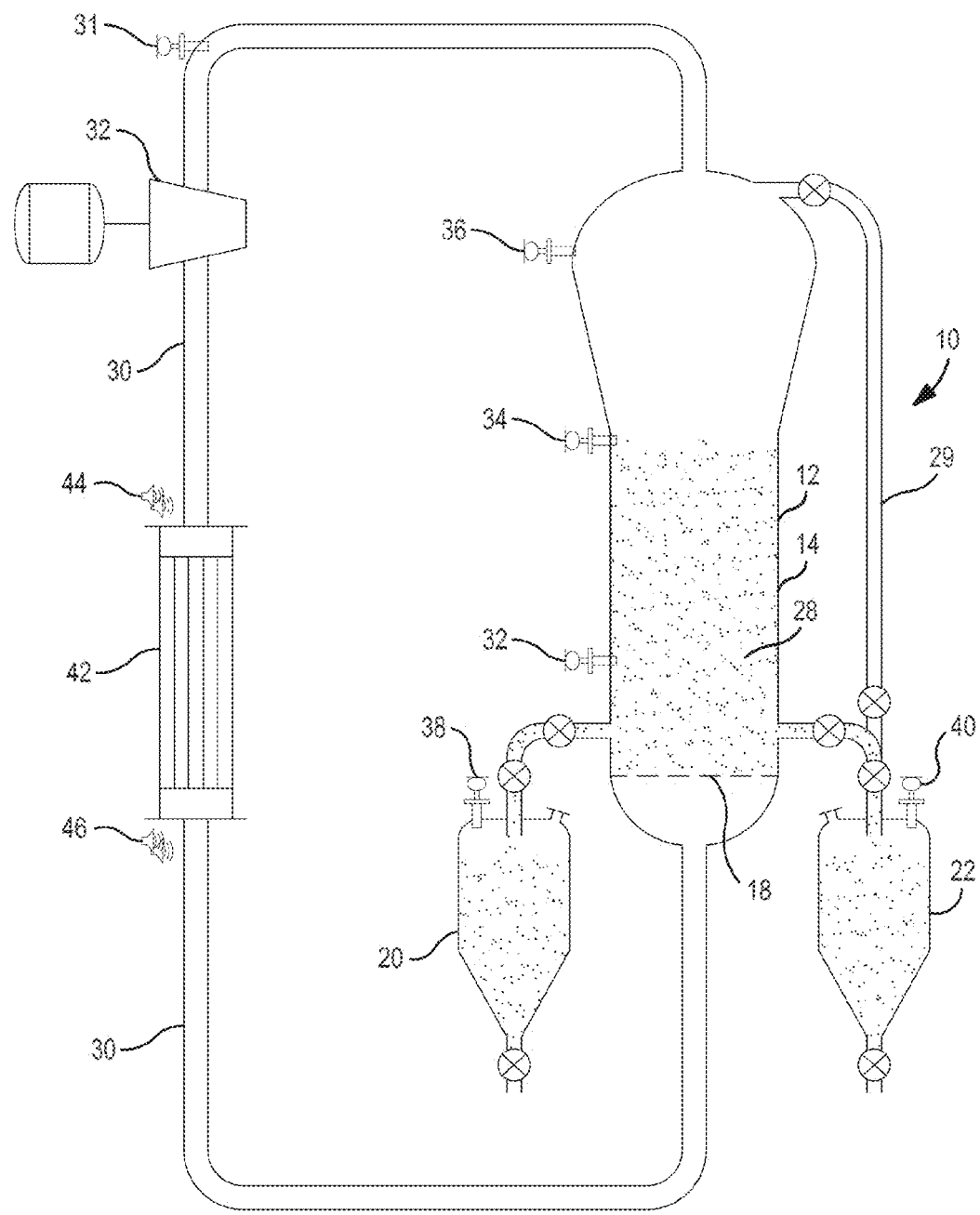
FIG. 9 depicts an embodiment of a conventional gas-phase fluidized-bed reactor system.
Figure 10:
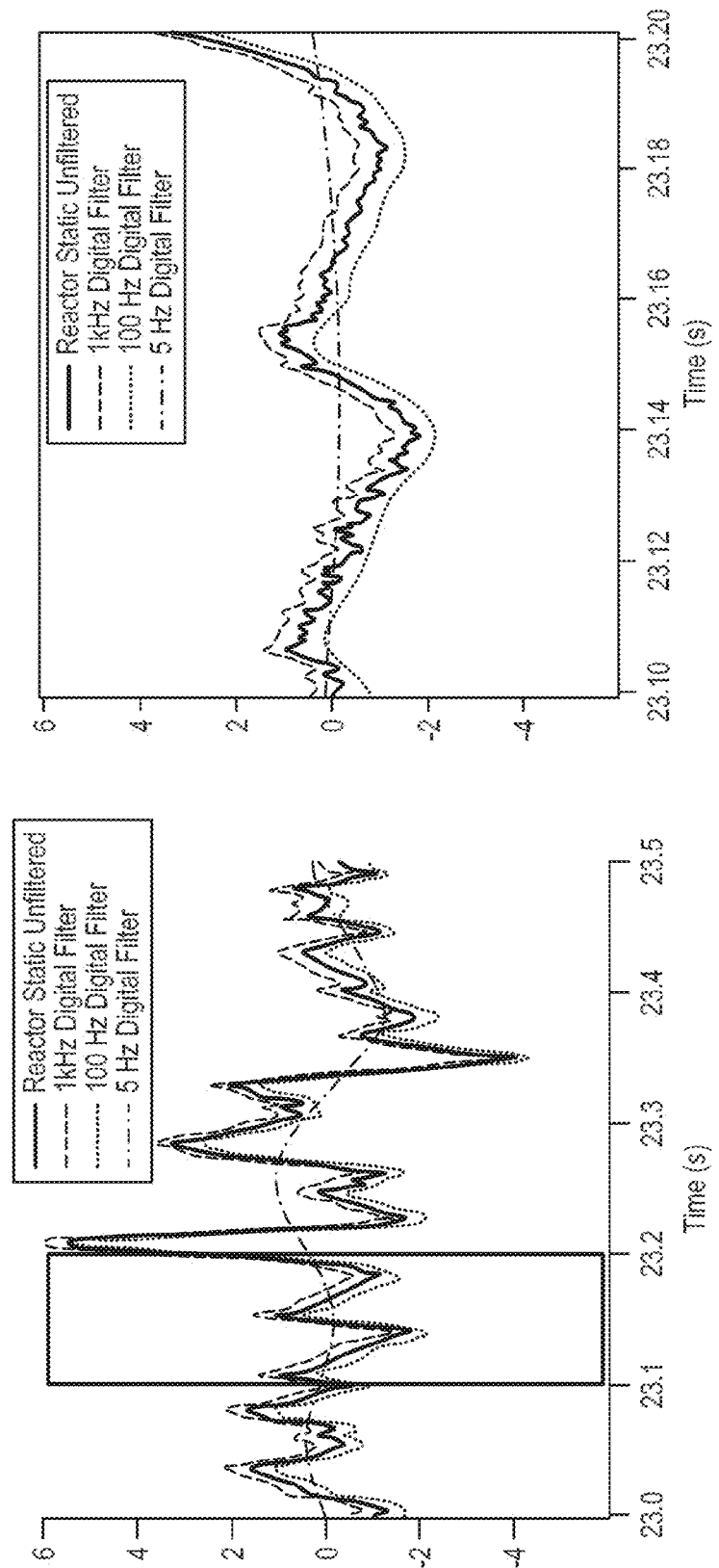
FIG. 10 is a double-plot in which the plot of FIG. 1 is split into components.

The unique coated static probe of the present disclosure can be used in the product discharge chamber in one aspect of the present disclosure. FIG. 9 shows product discharge tanks 20 and 22 used to remove product from a fluid bed reactor (components 12, 1, 4, 28 and 18). Coated static probes (38 and 40) located in the product discharge tanks (20 and 22) provide a means to accurately measure charge on the resin discharged as product from the fluidized bed reactor (components 12, 1, 4, 28 and 18). Without a coating on the probes the charge on the resin cannot be accurately measured because the resin flowing into the tank impacts the probe surface producing a significant triboelectric charging signal that can overwhelm the signal due to the charge on the resin. The data processing techniques described in this application provide a means to extract a quantity proportional to the charge on the resin discharged into the tank when a coated static probe is used. Changes in this quantity in each discharge cycle provide a means to monitor how the charge on the resin changes during reactor operation.

The use of coated static probes in the recycle system is another aspect of the current disclosure. FIG. 9 shows a coated static probe 31 located in the recycle line 30. Coated static probes 31 provide a means to monitor the charge on the particles entrained in the gas stream being recycled. Without a coating on the probe particles in the recycle gas stream impact the probe and produce a signal from triboelectric charging that can overwhelm the signal coming from charge on the particles passing the probe. When a coated static probe 31 is employed the data processing techniques described in this application provide a means to extract a quantity related to the charge on the particles flowing in the recycle line. Changes in this quantity in provide a means to monitor how the charge on the resin changes during reactor operation.

The aforementioned coated static probes can be used with product vessels and tanks including, but not limited to:
  Product tanks
  Purge vessels
  Holding vessels
  Shipping vessels (railcars, trucks, ships)

Electrostatic charge can be bulk, individual, or refer to sign of particles passing near tip of probe.

A preferred static probe is coated with a dielectric. The surface properties of the probe can be configured to measure specific physical and chemical processes. The coated probe substantially reduces noise and/or artifacts in signals transmitted. The coated probe essentially takes the form of an electrode, such as a metal rod with a modified surface. The probe can be configured to measure, among other things, electrostatic charge, changing or fluctuating electric field, bubbles in charged fluid beds, and detection of transient surface active species (gas, liquid, or solid) not normally present, or desired, in a given system (i.e., contaminants in a system).

In this embodiment, a static probe can be coated with an electrically insulating composition to mitigate triboelectrification of the probe arising from charge transfer from impinging particulates and therefore mitigate extraneous signals via charge saturation of the coating. Conventional measurement methods are not viable when particles impact an uncoated sensing element because of the resultant signal altering charge transfer due to the impacts.

In another embodiment, a static probe can be coated to measure the ambient DC (direct current) electric field by periodically blocking the field near the probe while also substantially preventing particle-to-surface interactions via purging of the sensing element with a flowing gas. Since a conventional probe can only measure a change in induced signal, the probe does not have the ability to measure a DC or constant field as they do not create a change in induced charge at the probe tip (the derivative of a constant field is zero, therefore no change. By alternately blocking the electric field from reaching the probe's sensing element and then removing the block, a changing electric field is created. Then a change in induced charge at the probe tip can be observed and calibrated to a known field strength. Accurately measuring the DC field is possible if particle impacts and unwanted charge transfer with the probe are prevented, such as purging with a flowing gas stream.

Without being bound by any particular theory, it is believed that in configuring a coated static probe, three material properties are important in optimizing the ability of a dielectric material to maintain a saturation charge. The properties are the following:

(1) Dielectric strength—determines the maximum electric field at which the material reaches electrical breakdown (also known as dielectric breakdown voltage).

(2) Surface and volume resistivity—determine the rate at which a material will discharge analogous to an RC circuit. Surface resistivity describes the amount of conduction across the surface, while volume resistivity describes the amount of conduction through the material. Typical values of resistivity are the following: Conductive<$10^4$, $10^4$>Dissipative<$10^{11}$, Insulating≥$10^{11}$ (ANSI-ESD Surface Units: Q; ANSI-ESD Volume Units: Ω-cm).

(3) Placement within triboelectric series—affects the amount and polarity of charge transferred due to contact and separation. Ideally no charge would transfer between two objects of the exactly the same material, although in practice some transfer usually occurs.

To optimize the dielectric material for maintaining a saturation charge layer and inhibiting tribocharging, the dielectric strength, surface and volume resistivity should all be optimized. Another factor can in some cases be relative placement within the triboelectric series. Importantly, the ideal dielectric material should be of high dielectric strength, and high volume resistivity. It is also desirable for the coating to be similarly placed within the triboelectric series as the material that would collide with it. The dielectric strength should be high enough so the material doesn't breakdown as the charge builds up. Surface and volume resistivity should be in the insulating range so that the charge builds up and does not decay too quickly.

Useful coating materials include, for example, polyethylene.

Coating of static probes can be carried out by any means known in the art. One method is to heat the static probe with a heat gun then submerge it into a bed of polymer particles with suitable melting point and adhesive properties (if desired, the probe can be heated with an oven to ensure uniform heating). The particles then stick to the probe. With the particles in place, they can then be heated to the point where they begin to "flow" using the heat gun. Once the particles have formed a uniform coating, the heat source is removed so the coating can harden. This process is commonly called a dip coating. Other known dip coating methods may also be used.

Acoustic probes measure energy transfer due to collisions and/or vibration. Ideal data acquisition for these probes would be high speed (>20 kHz) to allow for Fourier analysis to determine particle flux. The signal from these probes can be dominated by mechanical noise and tube waves. It would be desirable to have methods for filtering out such noise and waves.

RF Probes

In the present disclosure, we are utilizing a novel spark detector to detect discharges inside a commercial PE reactor. These reactors are typically operated at about 80 degrees C. and 20 atmospheres of pressure. No existing spark detectors such as the 3M EM Aware can survive in these conditions. Therefore we developed a custom RF probe that feeds through the reactor wall (shown in FIG. 11). The RF probe employs double pressure containment for extra safety because reactor gas leaks can be extremely dangerous. Reactor gas components include ethylene, hydrogen, and other potentially explosive components. Additionally, the electronics used to detect the RF events cannot be located within the reactive environment due to problems such as chemical compatibility of components, electronics stability, electronics failure, high and variable temperatures, spurious signal generation, and electrical energy input into a potentially explosive environment. The specialized technology which we employ to address these various issues around safety, spurious signal suppression, and overall performance is referred to herein as "hardened".

For a suitably hardened probe configuration, we can utilize existing commercial spark detection electronics such as the EM Aware, or utilize a specially designed set of electronics. In the case of specially designed electronics, circuitry with high sensitivity and high speed electrical response is required along with a suitable discrimination circuit such as a single channel analyzer and/or frequency based filter circuitry. Lock-in amplification, for example, can be used to select a narrow frequency range in the presence of significant noise. Post processing can also be used to filter out unwanted signals using techniques such as Fourier analysis and digital filtering or correlation methods.

The probe sensing tip, or antenna, is also an important component in our design. Most notably, the probe cannot be located too close to metal surface such as a reactor wall, flange or other grounded metal surface. The probe sensitivity is also tunable as the sensitivity is proportional to the antenna length within the reactor environment. This antenna length, however, must not be too great as to interfere with the fluidized bed operations or present a surface that is prone to fouling due to its size, shape, and or location within the reactor environment.

In one embodiment of the probe, the RF antenna was connected using coax to the receiver/amplifier electronics located in an electromagnetic interference (EMI)-shielded and cooled enclosure outside the reactor. Effective EMI shielding required pi filters on the dc power supply lines at the shield surface to block spurious radio signals carried into the enclosure by the dc lines. The receiver/amplifier filter and threshold settings were optimized for the reactor electrical environment. A custom data acquisition program was written to monitor and record the spark counts and intensities.

Figure 11:
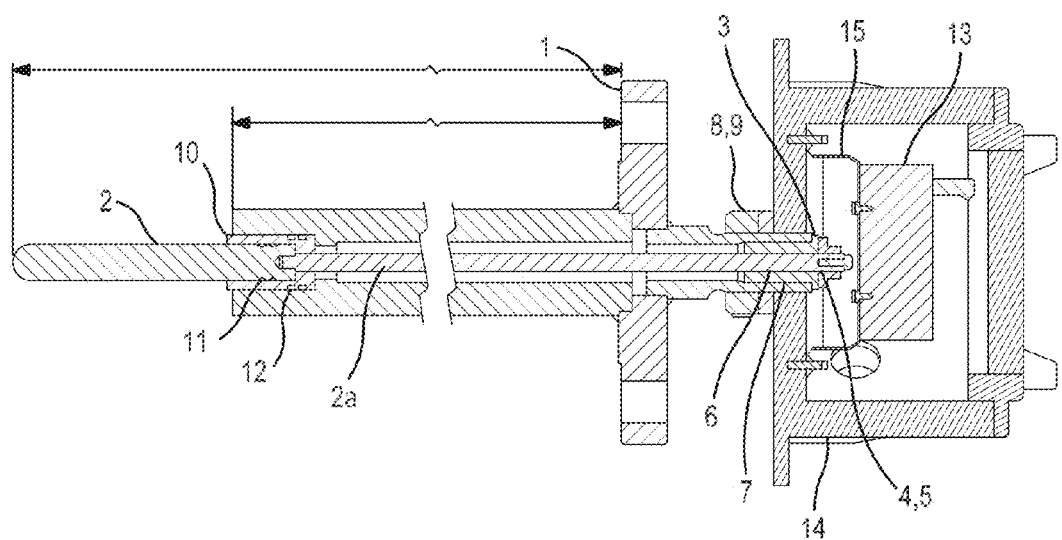
FIG. 11 is a representative cross-section of a custom RF probe for high temperature, high pressure reactor.
Figure 14:
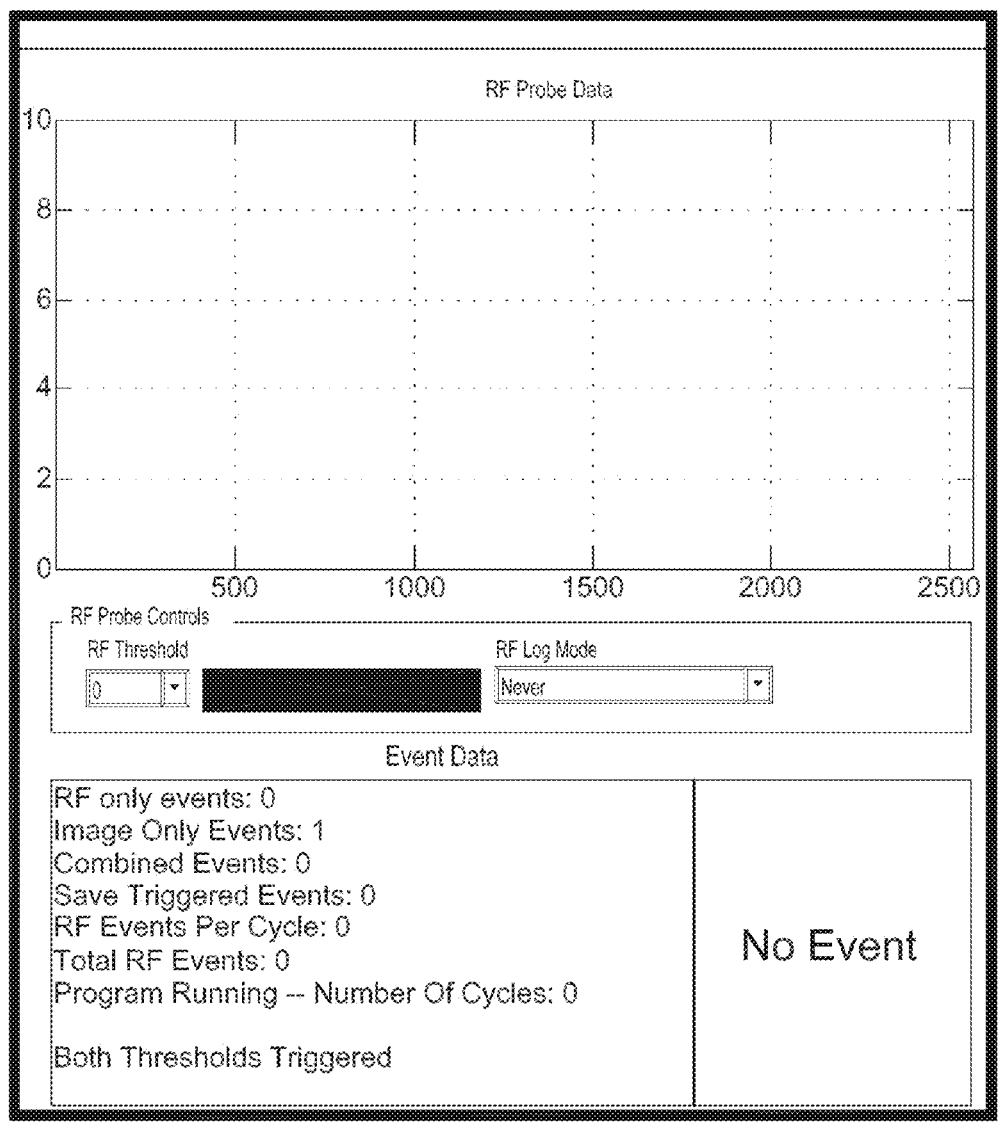
FIG. 14 is a screen shot of the custom program developed for the RF Probe.

The schematic drawing of an example of the hardened RF probe is shown below in FIG. 11. The probe contains a flange (1) that is bolted to the mating flange welded on the outside of the reactor wall. A large section of the probe assembly (2, 10, 11, 12) protrudes inside the reactor volume. In this embodiment, the probe is comprised of a solid metal cylindrical rod antenna (2) connected to a metal rod (2a) that feeds through the reactor wall and flange (1). This rod (2a) is hermetically sealed, using high-strength, high-temperature-rated insulating materials such as fiberglass (10) and Peek (3), to the flange housing in order to keep the antenna electrically isolated from the grounded flange (1); while also being able to pass high-pressure testing. Both ends of the rod (2a) are threaded: one attaches to the antenna (2) and the other accepts a washer (4) and jam-nut (5) which attaches the center conductor of a coax cable to the rod (2a). In one embodiment of the antenna assembly, the electronics module (15) is installed in the secondary pressure containment housing (14). The housing (14) is located outside the reactor, and is attached to the flange (1) using threaded nuts (8, 9). Viton O-ring (6) is used as part of the secondary pressure seal. A dc power supply (13) for the module (15) can also be optionally installed in the housing (14). In this embodiment, the presence of the electronics module (15) in the housing (14) necessitates cooling it when ambient temperatures are high. In an alternate embodiment of the antenna assembly, the electronics module and dc power supply are located in a separate shielded, cooled external enclosure. The antenna is connected to the electronics using coax cable that is run through metal conduit connecting the housing (14) to the shielded external enclosure.

The unique RF probe of the present disclosure exhibits the following properties:
Can use modified commercial, or custom electronics
Electronics can be internal, close coupled, or remotely located.
RF Probe detects electrical discharges of various types
Unique elements:
  i. "Hardened" safe design in challenging environments
  ii. No gas leaks; no ignition hazards
  iii. Containment
  iv. Temp regulation of electronics to ensure stability of response
  v. Filter power and shield electronics to prevent RF noise in commercial environment which contains spurious RF.
  vi. Electrode (antenna) designed to increase sensitivity while minimizing fouling
  vii. RF Probe coupled to Fluid Bed Reactor
  viii. RF Probe in Discharge Tank
  ix. RF Probe in Recycle Line
  x. RF Probe in Product Tanks, Purge Vessels, as well as process lines, and general chemical reaction or other process vessels.
  xi. RF Probe in holding or shipping vessels such as railcars or trucks.
  xii. RF Probe for use in a chemical plant, refinery, or other field-based or mobile hydrocarbon processing facility such as an offshore rig or marine vessel.

Bench Testing of the RF Probe

A small spark gap generator was fabricated as shown in FIG. 12a. This spark gap was attached to the end of the 21-foot tube as shown in the right side of FIG. 12b. FIG. 12b also shows the circuit which contains a 10 kV DC power supply connected to a ~1 TΩ adjustable resistor in series with the spark gap. The resistor is a wooden dowel with alligator clip electrodes clipped to it with various separation distances. The resistance is adjusted by changing the separation distance. The resistance controls the repetition frequency of the spark by changing the charging current to the capacitance of the electrodes. A capacitor can also be added to increase the energy of the spark by simply coating the wire with aluminum foil and attaching it to ground, but the tests here created the smallest spark possible without the capacitor.

The energy of the spark was determined by first measuring the breakdown voltage of the gap by ramping up the voltage until the gap sparked. This was found to be 8.1 kV. The amount of charge in the spark was determined by applying a known voltage (1000 V) across the spark gap (disconnected from ground) and then approaching one electrode with a grounded probe. The grounded probe was connected in series with a Keithley 610B Electrometer to measure the charge transferred. Once the charge was found, the capacitance of the gap was determined using $C=Q/V$. The capacitance was found to be 13 pF. The energy of the spark is approximately $\frac{1}{2}CV^2$, where V is the voltage at breakdown (8.1 kV). The calculated energy was 417 µJ.

Measurements of the RF signals generated by the sparks were recorded using the RF Probe with the 3M EM Aware electronics module. A low-light video camera was also used to verify that a spark occurred. A data acquisition program was written so that logs of spark events could be recorded. An example of the output text file is shown in the FIG. 13 below. The name of the file contains the date and time of an RF event. Using the recommended camera exposure time of 500 mS yields a log file that recorded for 0.5 seconds. The file contains the trigger type and how the event was triggered, as well as data for all the RF sparks that occurred during that 0.5 second period. The RF probe signal magnitude of each spark is given in volts (4.3962 in this case). Exposure time, camera temperature, and binning parameters are also given in the data file.

Custom Data Acquisition and Control Program

Figure 4:
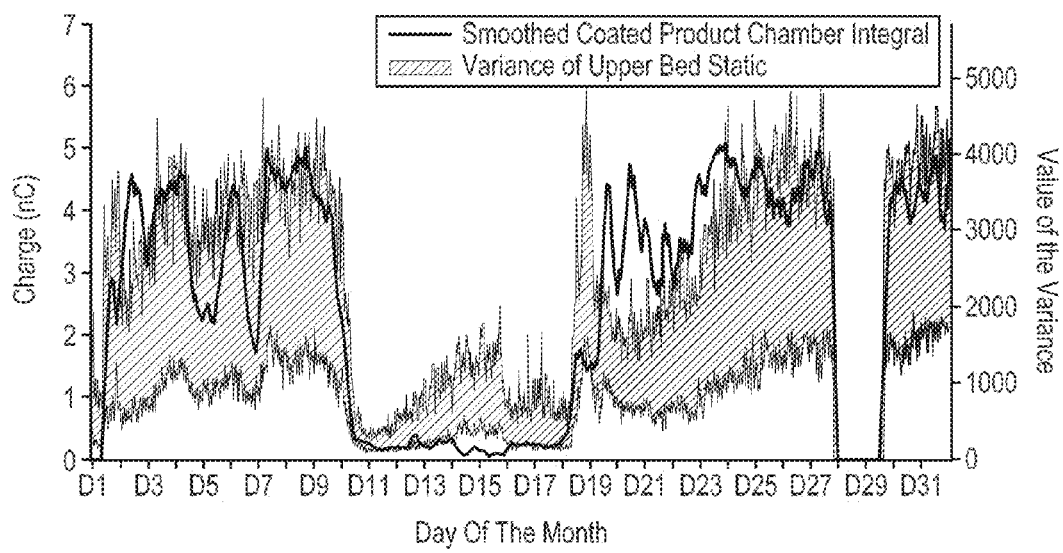
FIG. 4 is month long plot of the variance of the upper bed static vs. the charge calculated from the product chamber discharge integral.
Figure 5:
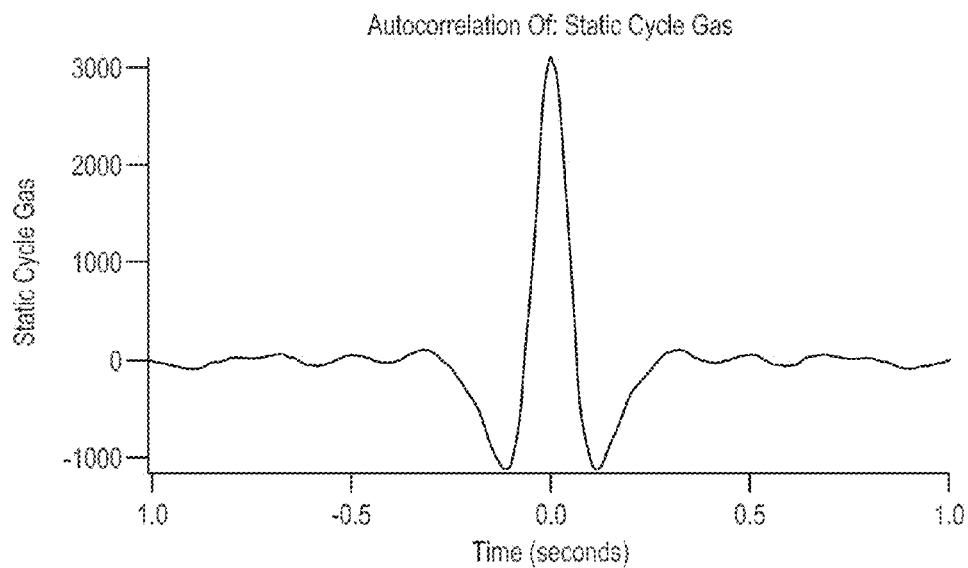
FIG. 5 is a plot of the center of the autocorrelation of the recycle line static probe signal.

The custom DAC program that takes the images, monitors and controls the RF Probe and saves the data is written in MATLAB and run from within the MATLAB environment. Once the program is loaded, the editor appears and the graphical user interface (GUI) can be started by clicking on the green play button. The screenshot of the GUI is shown in FIG. 4 below.

RF Probe Data—The signals from the RF Probe are displayed in the RF Probe Data box. The bottom scale is time and the y-axis is the ESD event magnitude in volts. All of the ESD event processing is performed within the RF Probe using the EM Aware® electronics module. The 4.20 mA output of the EM Aware® from the RF Probe is converted into a 0-10 volt signal using a Burr-Brown RCV420 DIP chip which is read by the National Instruments DAQ A/D connected to the computer using the PCI bus. The NI DAQ board is a model PCI-6259 and is controlled from within the MATLAB program.

RF Probe Controls—The RF Threshold can be sent remotely using this box on the GUI. The threshold magnitudes range from 1 to 10 can be controlled by the user. Once a threshold is chosen, the user clicks "Send to RF Probe" and a voltage output from the NI DAQ D/A connected to the computer is converted to a 4.20 mA signal using an external Burr-Brown XTR110 DIP chip. A corresponding verification signal is sent back from the RF Probe and is displayed in the RF Probe Data box.

RF Log Mode—The RF Log Mode is designed to store RF Data for long periods of time. It can be triggered to save data Always, Only When Triggered, or Never. The result is a small text file (shown in FIG. 3) that outputs the event magnitude date and time stamp. Each subsequent event is appended to that file.

Trigger Mode—RF data is stored for every event. Trigger occurs for the RF probe when events occur that are larger than the threshold set by the user in the RF Probe Controls box.

Sound—The user has the option to have a sound output when an event occurs. All events cause the large square green "No Event" to change to a red "Event" display.

Event Data—The Event Data box displays a running total of the number of RF Events triggered, Saved Triggered Events, RF Events per Cycle, Total RF Events and whether the program is running or not. It also displays the current state of the program.

Conventional Gas-Phase Fluid Bed Reactor

FIG. 9 depicts an embodiment of a conventional gas-phase fluidized bed reactor system 10. System 10 has a gas-phase reactor 12 employing a recycle stream 30 for unreacted gas and solids. Reactor 12 typically has a bed 14, an expanded section 16, a distributor plate 18, a first product chamber 20, a second product chamber 22, and product conduits 24 and 26 for conveying product to chambers 20 and 22, and an enhanced fill line 29. The enhanced fill line is defined any part of the product discharge system that is used to permit unreacted gas and fine particles to return to the reactor system. During operation, reactor 12 contains a solid phase 28, typically a catalyst. A reactant gas (not shown) is passed through distributor plate 18 through solid phase 28 in bed 14 and out of expanded section 16 into recycle stream 30. Recycle stream 30 has a compressor 32 and a heat exchanger 34 (such as a cooler) there along for pressurization, transport, and temperature modification of the reactant gas prior to return to reactor 12. Enhanced fill line 29 permits gas (and tiny particles entrained therein) to be recycled from product chamber 22 to the top of reactor 12. In another embodiment, a second, analogous enhanced fill line (not shown) could be employed between product chamber 20 and the top of reactor 12. System 10 has static probes 31, 32, 34, 36, 38, and 40 positioned into reactor 12 approximately at bed 12, the upper region of bed 12, expanded section 36, product chamber 20, and product chamber 22, respectively. System 10 has acoustic probes 38 and 40 positioned within the inlet and outlet, respectively, of heat exchanger 34. Precise placement, number and types of these probes can vary from reactor to reactor.

Fluidized bed reactor systems are disclosed by way of example in EP0784637 B2; EP0970970 B1; EP1623999 A1; EP2263993 A2; U.S. Pat. No. 6,660,812 B2; WO2005/113615 A2; and WO2002/06188 A2, all of which are incorporated herein by reference in their entireties.

In the method of the present disclosure a signal is received from a probe in contact with the interior of the reactor or a process component in communication with the reactor. The signal can be measured by a variety of measurement techniques and equipment, including amplifiers, filters, analog-to-digital converters, oscilloscopes, and or a computer. After the signal from the probe is received, the signal is modified, processed, or analyzed by mathematical processing or signal analysis techniques. This processing can be done in real-time using a computer system or specialized hardware. The processing can also be done as a post-analysis step resulting in a time-lag between measurement and human ability to react. The processed result is derived, i.e., promulgated in response to, a physical property or condition within the reactor or a process component thereof, e.g., a recycle line or heat exchanger. Physical properties or conditions include fluctuating electric field, sign of passing individual charged particles, presence of transient surface active species, bubbles in charged fluid beds, bubble size, bubble transit time, particle flux, gas velocity, and or mass flow. After the signal has been modified, one or more operating parameters of the reactor are adjusted if the value for the physical property or condition is different than a desired or predetermined value. The desired or predetermined value may be a constant or may be variable-dependent or an algorithm or operator input.

Specialized Instruments for Measuring Static

Also disclosed herein are instruments, and their design, for measuring and/or monitoring electrostatic phenomena within a gas-phase, fluidized-bed reactor. These instruments are used to make adjustments within the reactor to minimize electrostatic forces so as to improve performance and reduce negative effects, such as fouling and material carryover into the recycle system. These instruments function by measuring a particular electrostatic parameter such as, but not limited to, charge, electric field, and/or current; and then suppressing spurious signals such as tribocharging due to particle impacts, through specialized instrument design and data analysis methods.

In one form, the specialized instrument is a coated or uncoated static probe for measuring electric field and or particle charge state.

In another form, the specialized instrument is an oscillatory electric field probe for measuring electric field.

In yet another form, the specialized instrument is a chopped electric field probe for measuring electric field.

In yet another form, the specialized instrument is a radio-frequency antenna probe for detecting electrostatic discharges.

The following are examples of the present disclosure, and are not to be construed as limiting.

EXAMPLES

In the present examples, mathematical techniques have been applied to a specific fluidized bed, gas phase, polymerization reactor system. This reactor is equipped with multiple static and acoustic probes. Some of the static probes are commercially available bare-metal probes. Other static probes have been intentionally surface modified through the application of a dielectric coating.

By way of example, a typical fluidized bed, gas phase polyethylene reactor operates at approximately 300 psi and 85 degrees C. with a feed gas composition dependent upon the desired product but largely composed of ethylene. Important components of the reactor system include the main reactor vessel, the fluidized bed, a distributor plate at the bottom of the bed, a disengagement zone above the bed, a recycle gas system, a compressor, a heat exchanger, and a product discharge system. Static probes are available, for example, from Progression, Inc., and are described in U.S. Pat. Nos. 6,008,662 and 6,905,654, which are incorporated herein by reference. Acoustic probes are available, for example, from vendors such as Process Analysis and Automation, LTD. These vendors provide proprietary hardware and software for measuring their probe signals.

Processing Techniques and Interpretations

Fourier Analysis and Digital Filtering of Raw Fast Data from Static Probes

Fourier analysis is a typical mathematical technique for isolating frequency components of a waveform, making it easier to manipulate the base components of the waveform. Equation 1 is a summation form of a Fourier analysis technique that takes into account the imaginary components of the waveform.

$$s_P(t) = \sum_{k=-\infty}^{\infty} S[k] \cdot e^{i2\pi \frac{k}{P} t} \quad (1)$$

The variables are defined as follows:
 $S_P(t)$: a periodic function wherein t is time
 P: the period of periodic function $S_P(t)$
 S[k]:, where k is frequency This Fourier analysis technique converts an amplitude versus time spectrum to an amplitude versus frequency spectrum, which can then be modified using a digital filter. In this instance, the digital filter is another waveform with a sharp transition to zero at the maximum frequency that is desired. Once the filter has been applied, the inverse Fourier transform is applied and the frequency components outside of the filter no longer exist.

Data was collected at a rate that is comparable to the timescale of particle-probe interactions in the reactor. Examples of particle-probe interactions are current induction due to particles passing by the probe tip and charge transfer due to particle impacts. For purposes herein, we refer to this signal simply as a "static signal". Based on gas velocity and material properties of the particles and probes, the timescale of a particle-probe interaction is 10 msec or 100 Hz. In current industry practice, data from static probes is collected at 100 Hz or less, with a low-pass filter roll-off of 5 to 20 Hz. Frequencies above the roll-off value are sharply attenuated.

Data with a 5 to 20 Hz roll-off is too slow to see particle-probe interactions as displayed in FIG. 1. Fast data was taken directly from the probes at 100 kHz and analyzed using Fourier analysis (Equation 1) and digital filtering. The analysis shows that for most of the static probes, if the data acquisition rate is at least 100 Hz, particle-probe interactions are visible. The 100 Hz filtered data in FIG. 1 clearly follows the short time scale bipolar transitions contained within the traces sampled at faster rates of 1 kHz and 10 kHz. These short timescale transitions are individual positive and negative amplitude fluctuations, which are interpreted as either particle impacts or the charge of particles passing by the probe. The 5 Hz trace does not follow the short time scale fluctuations which are characteristic of these phenomena. The 5 Hz trace exhibits roll-off, which limits the amplitude and resolution, therefore making it unreliable for measuring particle impacts or the charge of particles passing by the probe.

Another type of event that has been shown to occur in the reactor and can be analyzed using these same methods on the static probe data is electrostatic discharges. Electrostatic discharges occur on a timescale of hundreds of nanoseconds requiring data acquisition rates on the order of MHz or GHz. In this case, the static probe is used more as an antenna to detect radio-frequency discharge events within the reactor.

Product Chamber Static Integration

Figure 2:
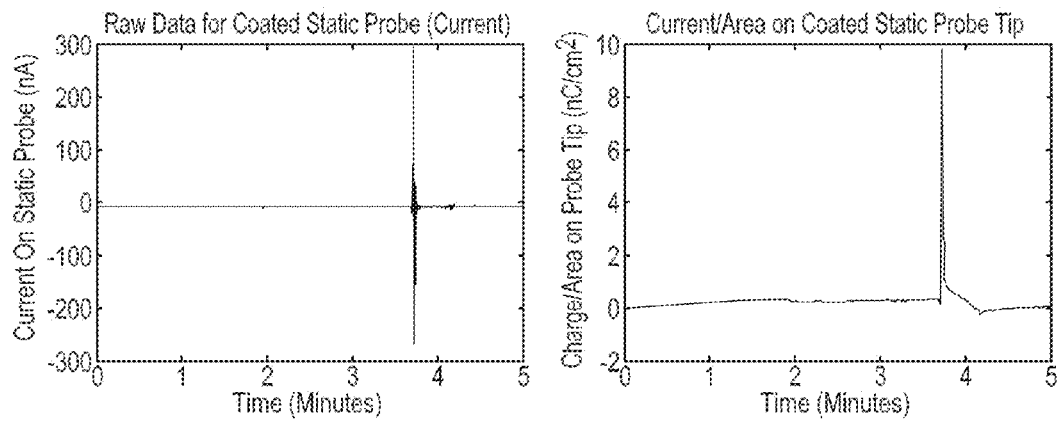
FIG. 2 is a plot of raw current data from the coated product chamber static probe (left) and acquisition rate and surface area compensated integral or charge (right).

A set of probes, referred to as the product chamber static probes are located outside of the main reactor vessel in the product chambers. Approximately one ton of the product is discharged to the chambers in one product discharge event. The product discharge event is easily seen in the data in both plots in FIG. 2 as an amplitude change occurring between 3 and 4 minutes on these plots.

The static probe is located at the top of the product chamber near the opening where the particles are discharged into the chamber. The uncoated static probe measures current induced on a sensing tip due to charged particles passing by and is also susceptible to triboelectric charge transfer from particle impacts with the probe. In order to minimize spurious signal arising from triboelectric charge transfer due to particle impacts, the product discharge chamber probes can be coated with a dielectric coating of polyethylene to mitigate tribocharging. In this case, the induced probe current due to the changing electric field generated by the charged particles entering the chamber can be measured and the charge in the chamber calculated. The measured current from the static probes has units of amps. As Equation 2 indicates, the integral of current over a definite time yields the charge, $$Q = \int_{t_i}^{t_f} I \, dt \quad (2)$$

wherein I=current in Amps, t is time in seconds, and Q=charge in Coulombs.

The electric field due to the resin in the reactor is related to the charge on the resin assuming the charge density in the reactor is uniform. The general equation for determining electric field is set forth below as Equation 3:

$$E = \frac{1}{4\pi\varepsilon} \int \frac{\rho}{r^2} \hat{r} \, dV \quad (3)$$

The variables are defined as follows:
 E: Electric field
 V: volume within reactor
 $\in$: permittivity of material within volume (can be approximated as $\in_o$ for gas environment)
 ρ: charge density
 r: distance from center of charge density The specific equation for determining the radial electric field within a cylindrical reactor, and uniform charge distribution, is given below as Equation 4 (variables similarly defined as in 3 above):

$$E(r) = \frac{\rho r}{2\varepsilon} \quad (4)$$

Electric field arising from the charged resin indicates the overall charge state of the reactor. The long period charge signal from the product chamber has been shown to be inversely correlated to the amount of "co-feed" or antistatic that is added to the reactor.

Monitoring of the average DC baseline value can also provide an indication of the average triboelectric charge transfer to the probe, which can also prove useful in detecting particle type changes, or probe coating changes.

Time-Resolved Means of Recycle Line Static and Acoustic Probe Signals

The long-term mean is calculated using Equation 4 wherein "n" is small but is repeated for many iterations.

$$\bar{x} = \frac{1}{n} \cdot \sum_{i=1}^{n} x_i \quad (4)$$

Variables defined as:
 $\bar{x}$: mean of a set of values
 x: set of values
 n: length of set x
 i: iterator Recycle Line Static Static probes are susceptible to charge transfer due to particle collisions. The mean signal is the DC signal and is an indication of the charge transfer from particles to the probe, therefore the mean signal is interpreted as particle flux. The mean can also give additional qualitative information. The sign of charge transfer is dependent on the materials that collide and the environment in which they collide. In this example, the charge transferred between the static probe and the particles is a net negative as seen by the probe.

Figure 3:
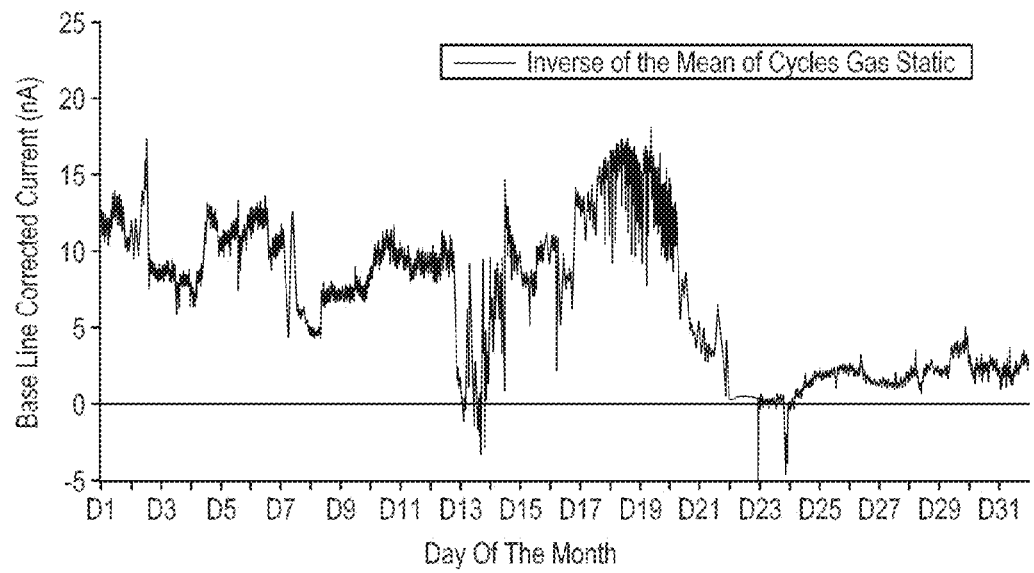
FIG. 3 is a plot of the inverse of the cycle gas or recycle line static mean.

FIG. 3 is a plot of the inverse of the recycle line static probe mean over a period of one month. The inverse of the mean is plotted in FIG. 3 to aid interpretation. The black line in the plot is the base line, and when the mean signal has a sharp transition toward the baseline (opposite of normal activity, often crossing over the base line), it is interpreted as due to a poison in the reactor. This interpretation has been shown experimentally through multiple poison events in a reactor as displayed in Table 1 below.

TABLE 1

| Date | Confirmed w/ Data |
|---|---|
| Sep. 11, 2011 | Yes |
| May 6, 2011 | Yes |
| Jan. 3, 2011 | Yes |
| Nov. 29, 2010 | Yes |
| Feb. 24, 2010 | Yes |
| Oct. 14, 2009 | Yes |
| Total | 100% |

A bare metal static probe, in the presence of contaminants, can experience multiple physical processes, each of which results in unique signatures in probe response. Contaminant species adsorbed by the colliding materials can change the sign of the triboelectric charge transfer.

In the case of contaminants that act as catalyst poisons, the inhibited polymerization productivity leads to an increase in the carryover of particles from the bed. This is dominated by smaller particles. If the bed is experiencing bipolar charging, these additional particles could become positively charged, resulting in a change in sign of the probe response. In the case of contaminant species that cause additional particles to stick to the probe tip, the probe response may show an increase in unipolar charge of the opposite sign.

To identify the dominant mechanism leading to the apparent change in static probe signal we must analyze fast data ($\geq 1$ kHz, fast enough to see individual particles) to extract the net polarity of particles interacting with the probe during normal operations and during a poison event in the reactor.

To improve the detection of poison events in the reactor, an algorithm taking into account calculated parameters can be created. Parameters of this algorithm can include the following: static probe current mean (the dc signal due to tribocharging) derivative of static probe mean, acoustic probe sound intensity mean derivative of acoustic probe mean, cycle gas velocity, catalyst grade (specifically transitions), production rate, reactor pressure, deviation from reactor set temperature, and catalyst feed rate.

Acoustic Probes

Acoustic probes measure the energy transferred from particles colliding with the reactor walls and plumbing. The mean of the acoustic probe signals in the recycle line is indicative of mass flow. Two acoustic probes can be employed, for example, to demonstrate feasibility.

Combined Approach

When the mean averages of the recycle line probe signals, static and acoustic, are inspected together, they reveal or confirm even more information the current charge state of the particles. The current charge state can be characterized according to the four following scenarios:

Scenario #1: Acoustic probe means are changing (increase or decrease) and the static probe means remains constant.
Combined Interpretation: Charge state of the particles is changing.
Scenario #2: Acoustic probe means remain constant and the static probe means are changing (increasing or decreasing).
Combined Interpretation: Charge static of the particles is changing
Scenario #3: All probe means are changing.
Combined Interpretation: Mass flow is changing but relative charge state is not.
Scenario #4: All probe means remain constant
Combined Interpretation: Mass flow and relative charge state remain constant.

Time-Resolved Variances of Main Vessel and Recycle Line Static and Acoustic Probe Signals The variance is calculated using Equation 4, wherein, "n" is small and repeated for many iterations.

$$\mathrm{var} = \frac{1}{n}\sum_{i=1}^{n}(x_i - \bar{x})^2 \qquad (4)$$

Variables defined as:
 var=variance
 x: set of values
 $\bar{x}$: mean of set x
 n: length of set x
 i: iterator Main Vessel Static Probes The time resolved variance of the static probes is the moving or fluctuating portion of the signal from the static probes. This fluctuating signal is associated with the induced charge from a changing electric field due to charged particles or bubbles passing the sensing tip.

The variance of the main vessel static probes correlates well with the electric field interpreted from the product chamber static integration as shown in FIG. 4. The variance of the main vessel static probes can then be interpreted as an unscaled version of the bulk electric field in the resin bed.

Recycle Line Static

The variance of the recycle line static can be generally interpreted as the fluctuation in flow rate of charge particles and has many variables associated with its meaning. The fluctuations in flow rate are caused by variables such as changes in gas flow velocity and turbulence, particle flux, and particle charge.

Acoustic Probes

The variance of the acoustic probes is interpreted as the particle flux and average momentum transfer from particles hitting the recycle line cooler.

Autocorrelation of Recycle Line Static

The Autocorrelation of a signal (Equation 5) is a mathematical tool used for finding periodic signals inside of a single structure, similar to Fourier analysis.

$$\hat{R}(k) = \frac{1}{(n-k)\sigma^2}\sum_{t=1}^{n-k}(X_t - \mu)(X_{t+k} - \mu) \qquad (5)$$

The variables are defined as:
 $\hat{R}$: Autocorrelation function
 X: any discrete process
 n: length of discrete process X k: and positive integer less than n
μ: true mean
σ²: variance
t: iterator The autocorrelation of the recycle line static yields the same macroscopic information as the variance but offers more information on a microscopic scale. The long term peak value of the autocorrelation is what is similar to the variance but the bipolar nature of the autocorrelation indicates that the signal is derived from particles that pass by the probe tip.

Peak of the Cross-Correlation of Acoustic Probes

Figure 6:
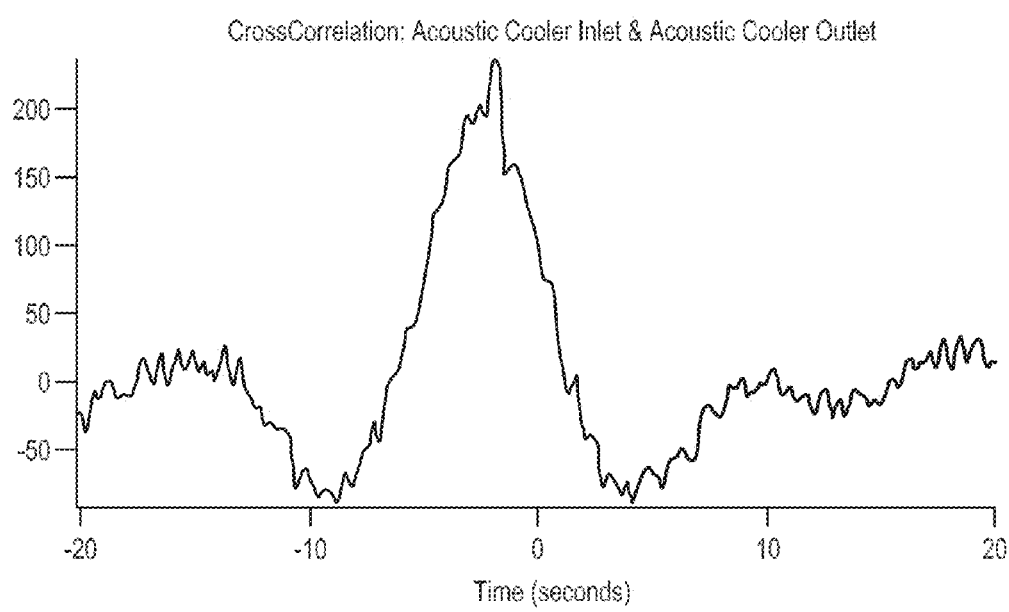
FIG. 6 is a plot of the center of the cross-correlation of the cooler inlet and outlet acoustic probes.

The cross-correlation is a measure of the similarity of two signals throughout time. Equation 6 is the summation form of the cross-correlation algorithm.

$$(f * g)[n] \overset{def}{=} \sum_{m=-\infty}^{\infty} f^*[m]g[n+m] \quad (6)$$

f or g: any waveform
f*: complex conjugate of f
n: shifts function g
m: iterative value or counter The location of the peak of the cross-correlation of the acoustic probes yields the transit time of the particles through the recycle line cooler. The peak in FIG. 6 is located to the left or negative side of the center of the cross-correlation. This indicates that the features of the signal from the cooler inlet acoustic occur before the features of the cooler outlet acoustic signal and that they are strongly correlated at that point. The interpretation is that the same particles that transfer energy to the cooler inlet acoustic probe transfer energy to the cooler outlet acoustic probe 2 seconds later. So the transit time of particles through the cooler is 2 seconds.

Cross-Correlation of Recycle Line Static with Acoustic Probes

Figure 7:
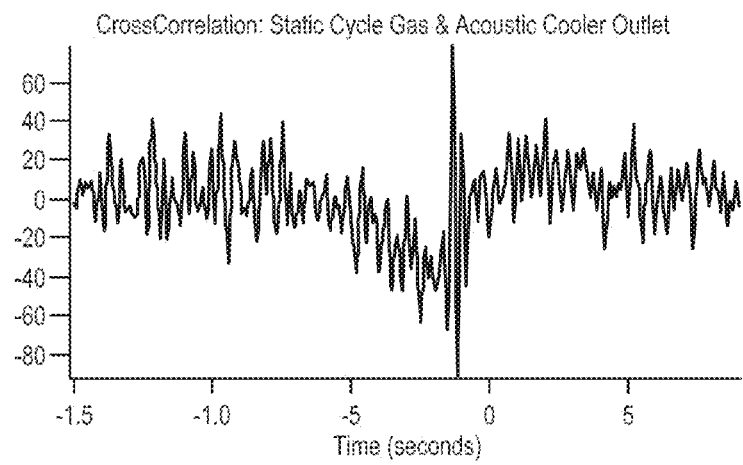
FIG. 7 is a plot of the cross-correlation of the recycle line static signal with the cooler inlet acoustic signal.

The peak of the cross-correlation of the recycle line static with the acoustic probes yields the transit time of particles in the recycle line. The cross-correlation between the recycle line static and the cooler inlet acoustic (FIG. 7) yields the recycle line gas velocity assuming the linear distance between the two probes is known. The tail of the cross-correlations indicates that not all of the entrained particles travel at the cycle gas velocity. The term "tail" is meant to indicate those relatively few particles that are correlated at a later time from the main population of particles.

Figure 8:
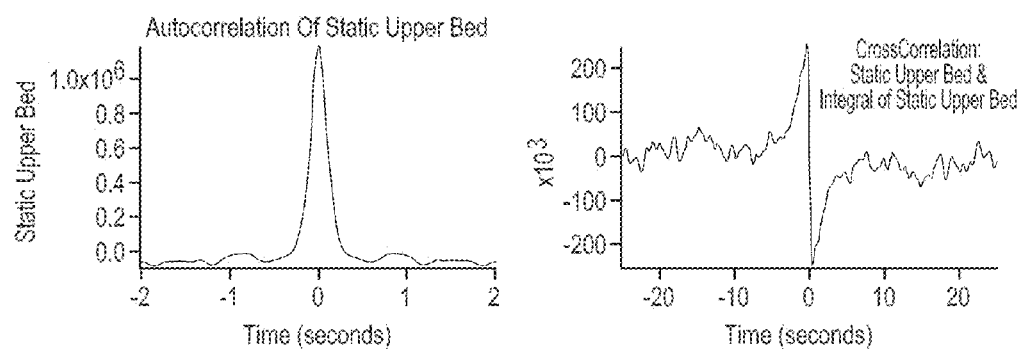
FIG. 8 is a plot of the autocorrelation of the upper bed static probe signal (left) and the cross-correlation of the upper bed static signal with its integral (right).

Autocorrelation of Main Vessel Static Probes and Cross-Correlation of Main Vessel Raw Static with their Integrals The two processing schemes, as shown in FIG. 8, indicate the movement of bubbles in the bed. The peak of the autocorrelation yields the size of the bubbles or the distance from the probe to the bubble. The offset of the two poles of the cross-correlation of main vessel static with its integral indicates the transit time of the bubbles.

Correlation of Product Chamber Static Integration with Short Term Peak Finding in Recycle Line Acoustic and Static Sensors Fluidized bed reactors with modified product discharge systems can have a greater distributor plate fouling rate than other reactors of similar size and production rate. The increased plate fouling is due to the modified product discharge system's fill-line return to the top of the reactor. The modified fill-line allows for pressure equalization of the product chamber resulting in better fill rates of the product discharge tanks. Particles are then entrained in the gas and carried up the modified fill-line and potentially entrained into the recycle line. These entrained particles can potentially where they end up at the distributor plate where they get stuck but continue to polymerize causing them to grow and foul the distributor plate. Any increased entrainment of particles is potentially detectable on a static probe installed into the cycle gas line. However, in practice it is very difficult to see a change in the raw static probe signal on a short timescale because the variance of the data is three orders of magnitude larger than the mean.

Product discharge events can be used as time reference points for other analyses. For example, the front point of inflection of the peak of the integral of the product discharge static probe current signal indicates the beginning of a discharge to the product chamber. Using this as the starting point to look for increases in the short period mean value of the recycle line static and acoustic probes will determine if extra particles are entrained in the recycle line due to operation of the improved product discharge system (IPDS) or enhanced fill line. The enhanced fill line permits gas (and tiny entrained particles) to be recycled from the product chamber to the top of the reactor.

The short period mean averages (of the recycle line static and acoustic probe signals) indicate that approximately 20 percent more particles are detected by the probes roughly 30 seconds after a product discharge event.

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A coated static probe which monitors the electrostatic charge on particles entrained in the gas stream of a vessel, said probe comprising:
   an electrode with a modified surface comprising an electrically insulating coating, thereby mitigating triboelectrification of said probe arising from charge transfer from impinging particulates and extraneous signals via charge saturation of said coating.

2. The probe according to claim 1, wherein said coating is a dielectric material that maintains a saturation charge layer and inhibits tribocharging.

3. The probe according to claim 2, wherein said dielectric material is a high dielectric strength, and high volume resistivity.

4. The probe according to claim 2, wherein said dielectric material is at least one material selected from the group consisting of: polyethylene, polypropylene, polytetrafluoroethylene, polyether ether ketone, aluminum oxide, silicon dioxide, iron oxide, and any other electrically insulating material.

5. The probe according to claim 2, wherein said dielectric material maintains said charge saturation by exhibiting at least one property selected from the group consisting of: dielectric strength, surface and volume resistivity, and placement within triboelectric series.

6. The probe according to claim 5, wherein said dielectric strength determines the maximum electric field at which the material reaches electrical breakdown.

7. The probe according to claim 5, wherein said surface and volume resistivity determines the rate at which a material will discharge analogous to an RC circuit.

8. The probe according to claim 5, wherein said placement within triboelectric series affects the amount and polarity of charge transferred due to contact and separation.

9. The probe according to claim 1, wherein said coating is applied to said static probe by dip coating.

10. The probe according to claim 9, wherein said dip coating comprises the steps of:
heating said static probe;
submerging said heated static probe into a bed of polymer particles with suitable melting point and adhesive properties, such that said polymer particles adhere to said static probe;
heating said static probe after said polymer particles have been adhered thereto to the point where they begin to flow; and
once said polymer particles have formed a uniform coating on said static probe, heating is stopped, thereby allowing said coating to harden on said static probe.

11. A method for monitoring the electrostatic charge on particles entrained in the gas stream of a vessel comprises: disposing said coated static probe according to claim 1 within said gas stream of said vessel.

12. The method according to claim 11, wherein said gas stream is at least one stream selected from the group consisting of: a product discharge stream, a recycle stream, a fluidizing gas stream, a mixing stream, a purge stream, a feed stream, and a transfer stream.

13. The method according to claim 11, wherein said vessel is at least one vessel selected from the group consisting of: a fluidized bed reactor, a product tank, a purge vessel, a holding vessel, a shipping vessel, a discharge tank, a mixing vessel, piping between said vessels, a shipping vessel, a rail car, and a truck.

14. A coated static probe which monitors the electrostatic charge on particles entrained in the gas stream of a vessel, said probe comprising:
an electrode with a modified surface comprising a coating which measures the ambient direct current electric field by periodically blocking the field near said probe while also substantially preventing particle-to-surface interactions via purging of a sensing element with a flowing gas.

15. An RF probe which monitors electrostatic discharges in a vessel, said probe comprising:
an antenna;
a flange bolted to a mating flange welded on the outside of a wall of said vessel;
an electrode connected to said antenna, wherein said rod is hermetically sealed by means of an insulating material, thereby electrically isolating said antenna from said flange;
an electronics module and a power supply disposed within a pressure containment housing or a separate shielded, cooled external enclosure located outside of said vessel and electronically connected to said rod; and
an electrically conductive wire which electronically connects said antenna to said electronics module.

16. The RF probe according to claim 15, further comprises a double pressure containment housing.

17. The RF probe according to claim 15, wherein said probe is a hardened probe comprising: (a) spark detection electronics, or (b) circuitry with high sensitivity and high speed electrical together with a single channel analyzer and/or frequency based filter circuitry.

18. The RF probe according to claim 17, wherein said frequency based filter circuitry is at least one selected from the group consisting of lock-in amplification, Fourier analysis, digital filtering and correlation methods.

19. The RF probe according to claim 15, wherein probe sensitivity is proportional to the length of said antenna.

20. The RF probe according to claim 15, wherein said wire is a coax cable and said electronics module comprises a receiver/amplifier filter.

21. A method for monitoring the electrostatic discharges in a vessel comprises: disposing said RF probe according to claim 15 within said vessel.

22. The method according to claim 21, wherein said gas stream is at least one stream selected from the group consisting of: a product discharge stream, a recycle stream, a fluidizing gas stream, a mixing stream, a purge stream, a feed stream, and a transfer stream.

23. The method according to claim 21, wherein said vessel is at least one vessel selected from the group consisting of: a fluidized bed reactor, a product tank, a purge vessel, a holding vessel, a shipping vessel, a discharge tank, a mixing vessel, piping between said vessels, a shipping vessel, a rail car, and a truck.

24. A probe which monitors the electrostatic state in a vessel, said probe is at least one selected from the group consisting of: an oscillatory electric field probe, a chopped electric field probe, and a radio-frequency antenna probe.

25. A fluidized bed reactor comprising either a coated static probe or a radio frequency (RF) probe disposed in at least one portion of the fluidized bed reactor selected from the group consisting of: a recycle line, product discharge system, fluid bed, expanded or disengagement zone above the fluidized bed, purge system, and product handling or shipping system.

26. A stirred, slurry or other type of reactor system with a coated static probe or a radio frequency (RF) probe disposed in said reactor system.

* * * * *